US007119891B2

(12) United States Patent
White et al.

(10) Patent No.: US 7,119,891 B2
(45) Date of Patent: Oct. 10, 2006

(54) DETECTING SUBSTANCES IN DRINKING WATER RESERVOIRS

(76) Inventors: Brian N. White, 3132 Inverness Dr., Los Alamitos, CA (US) 90720; Charles Rockwell Booth, 6110 Avenida Cresta, La Jolla, CA (US) 92037; John H. Morrow, 5340 Riley St., La Jolla, CA (US) 92110

( * ) Notice: Subject to any disclaimer, the term of this patent is extended or adjusted under 35 U.S.C. 154(b) by 347 days.

(21) Appl. No.: 10/851,028

(22) Filed: May 21, 2004

(65) Prior Publication Data
US 2004/0233447 A1 Nov. 25, 2004

Related U.S. Application Data

(60) Provisional application No. 60/473,665, filed on May 22, 2003.

(51) Int. Cl.
*G01N 21/62* (2006.01)
(52) U.S. Cl. ................ 356/73; 356/317; 250/461.1
(58) Field of Classification Search ................ 356/73, 356/317, 318, 417; 250/458.1, 459.1, 461.1
See application file for complete search history.

(56) References Cited

U.S. PATENT DOCUMENTS 5,905,570 A * 5/1999 White et al. ................ 356/317

* cited by examiner

*Primary Examiner*—Gregory J. Toatley, Jr.
*Assistant Examiner*—Marissa J Detschel
(74) *Attorney, Agent, or Firm*—Greenberg Traurig LLP (57) ABSTRACT

The optical properties of water impounded in reservoirs such as large tanks with closed covers and in uncovered reservoirs are monitored to detect harmful substances. The system and method comprises illuminating the water with an artificial light source within the enclosure for monitoring of the reservoir. Radiance and irradiance fluxes are measured by one or more multiband radiometers. Changes in radiance and irradiance are used to calculate spectral attenuation coefficients of the water. Fluorescence spectra are measured. A computer look-up table of known absorption and emission spectra is compared to the spectral attenuation to determine if a substance has been detected.

18 Claims, 10 Drawing Sheets

|  | 225 | 254 | 285 | 300 | 325 | 350 | 375 | 400 | 425 | 450 | 475 | 500 | ORP | pH |
|---|---|---|---|---|---|---|---|---|---|---|---|---|---|---|
| Chlorophyll |  |  |  |  |  |  |  | A | A | AA | A | A | No | No |
| Chlorine Dioxide | A | A | A | A | A | P | A | A | A | A |  |  | Yes | No |
| Benzene | A | AA |  |  |  |  |  |  |  |  |  |  | No | No |
| Chloropyrifos | AA |  |  |  |  |  |  |  |  |  |  |  | No | No |
| Oxamyl |  | AA |  |  |  |  |  |  |  |  |  |  | No | No |
| Diuron |  | AA |  |  |  |  |  |  |  |  |  |  | No | No |
| Parathion |  |  | AA |  |  |  |  |  |  |  |  |  | No | No |
| Dinoseb |  |  |  |  |  |  | AA |  |  |  |  |  | No | No |
| Folic Acid |  |  |  |  |  | AA |  |  |  | F |  |  | No | No |
| Indoles |  | A | A | A | A |  |  |  |  | F |  |  | No | No |

DETECTING SUBSTANCES IN DRINKING WATER RESERVOIRS

RELATED APPLICATIONS

This application claims the priority date of the following U.S. Provisional Application: U.S. Ser. No. 60/473,665 entitled "DETECTING POISONOUS SUBSTANCES IN COVERED DRINKING WATER RESERVOIRS" filed on May 22, 2003, and incorporates by reference the entire contents of the above mentioned provisional application.

BACKGROUND

The present disclosure generally relates to the field of devices to monitor the safety of drinking water. More particularly, the disclosure relates to the field of water quality monitoring devices that are used to detect harmful agents that have been placed deliberately or come to occur naturally in water.

GENERAL BACKGROUND AND STATE OF THE ART

In view of the terrorist acts against the United States on Sep. 11, 2001, a new concern has now arisen wherein there is now a clear and present danger that foreign terrorists may seek to harm the world by deliberately placing poisons and other harmful agents into drinking water, including water stored in covered reservoirs.

Due to the cunning and viciousness of foreign terrorists, many known poisons and harmful agents can be deliberately placed into water in a manner in which the amount of poison or other harmful agent is so small as to be undetectable at the customer's tap by sight or smell. Further, many such poisons can he quickly dissolved in water, making detection by the consumer almost impossible only a short time after the poisons have been dispersed. Further, other regulated compounds and harmful agents can develop naturally in impounded water that are undetectable to the consumer.

One system to monitor the quality of water is disclosed in U.S. Pat. No. 5,905,570 issued on May 18, 1999, to Brian N. White and John H. Morrow and assigned one-half to the Department of Water and Power City of Los Angeles and one-half to Biospherical Instruments (hereafter the "'570 Patent"). The primary focus of the '570 Patent was to use a remote electro-optical sensor system to monitor the chlorophyll concentration in a water body. The body of water for which the apparatus and method of the '570 Patent were utilized was an open body of water such as a reservoir. In order for the system of the '570 Patent to operate, it was necessary that sunlight shine on the surface of the water body to provide the light needed for the apparatus to make the spectral measurements in the water column necessary to detect chlorophyll. One drawback of the '570 system is that it can only operate during daylight hours. While the system of the '570 Patent is very effective for monitoring chlorophyll concentration in water, it is not applicable to the problem sought to be addressed by the present disclosure.

Terrorists can place small quantities of a deadly poison into a water supply at night that can quickly dissolve and be distributed for human consumption long before the poison can be detected. This vulnerability is unacceptable. Further, harmful compounds other than chlorophyll can develop naturally in impounded water in concentrations that violate federal standards or public health goals. This situation is also unacceptable. Therefore, it is desirable to improve upon the '570 Patent to address the present problems and provide other advantages over other detection systems.

SUMMARY

A method and apparatus to detect poisons and other harmful agents that have been placed deliberately or developed naturally in drinking water stored in covered reservoirs is disclosed herein. One application for this method includes covered reservoirs because their relatively small size can make them a likely target for terrorist acts. However, the method and apparatus could apply to both covered and uncovered reservoirs alike.

This disclosure utilizes the optical properties of many anthropogenic compounds including commercial pesticides and poisons, petrochemicals and industrial dyes (collectively "poisons"), many naturally occurring drinking water contaminants including nitrate, nitrite, and natural organic matter (collectively "contaminants") and many microbes including algae and bacteria (collectively "biologicals"). Multiwavelength spectroradiometer(s) (i.e., multiband radiometers) are used to detect changes in the flux of an artificial light source illuminating reservoir water at characteristic wavebands. These changes, caused by absorption, scattering, and fluorescence of the light, are used to alert reservoir managers of the presence of new contaminants in the water.

In another aspect, the disclosure provides for multiband radiance or irradiance detectors, within a reservoir, placed in the vicinity of an artificial light source for detecting fluorescent poisons, contaminants and biologicals emitting light when exposed to sufficient excitatory radiation. Radiance is the optical flux of light flowing through a volume of a liquid, a solid, a gas, or a vacuum. Irradiance is the optical flux incident on a surface.

In another aspect, the disclosure uses spectral changes in the water column of a closed reservoir to differentiate as well as detect different poisons, contaminants and biologicals on the basis of their individual absorption and emission spectra. A reference table of absorbing and emitting wavebands provides the basis for an immediate operator alert that one or more known poisons, contaminants and biologicals may have been detected so that an appropriate command can be issued to prevent further distribution of water from the affected reservoir.

Continuous operation of an artificial light source in near ultraviolet and visible (UV-VIS) portions of the electromagnetic spectrum between wavelengths of 200 and 800 nanometers (nm) in the vicinity of multiband radiance or irradiance detectors provides broadband detection and differentiation of poisons, contaminants and biologicals in reservoirs twenty-tour hours a day. Thereby, corrective action can be taken.

As such, an apparatus and method is herein disclosed to continuously, automatically and efficiently monitor our nation's water supply to detect and differentiate various poisons, contaminants and biologicals and other harmful agents that have been placed deliberately or developed naturally in reservoirs and provide other features and advantages over present poison detection and contamination systems.

Further novel features and other objects of the present disclosure will become apparent from the following detailed description, discussion and the appended claims, taken in conjunction with the drawings.

DRAWINGS

Referring particularly to the drawings for the purpose of illustration only and not limitation, there is illustrated.

DETAILED DESCRIPTION

Although specific embodiments of the present disclosure will now be described with reference to the drawings, it should be understood that such embodiments are by the way of example only and merely illustrative of but a small number of the many possible specific embodiments which can represent applications of the principles of the present disclosure. Various changes and modifications obvious to one skilled in the art to which the present disclosure pertains are deemed to be within the spirit, scope and contemplation of the present disclosure as further defined in the appended claims.

The present disclosure is an application and method to monitor water that is housed in storage containers such as large tanks with closed covers, to detect expeditiously when a poison, contaminant or biological agent has been placed deliberately or developed naturally in a way that may cause injury or death to anyone who consumes the water, or that violates state or federal drinking water standards or public health goals. The monitoring of water may be continuous, essentially continuous, or performed at discrete time intervals.

A discovery of the disclosure is that many poisons, contaminants and biologicals absorb and/or emit ultra violet through visible (UV-VIS) light in characteristic ways. A reference table of the absorption and emission wavebands of specific poisons, contaminants and biologicals of concern can be used to detect and differentiate the presence of harmful agents so that appropriate action can be taken and contaminated water not distributed and subsequently consumed.

The present disclosure incorporates a remote electro-optical sensor (hereafter "REOS") system to provide continuous optical monitoring in the water enclosure. The REOS system of the present disclosure detects less than 10 micrograms per Liter (10 µg/L) of a strong, organic light absorber such as chlorophyll. The REOS system of the present disclosure detects less than 1 milligram per liter (1 mg/L) of a weak, inorganic light absorber such as chlorine dioxide. Scaled up to a one million gallon reservoir, these-detection limits correspond to less than an ounce to several pounds of applied material. Such small amounts of sabotage material could be carried up a tank ladder easily by an individual terrorist.

The amount of light absorbed by a solution is related to the optical properties of the constituents in accordance with a well known formulation known as Beer's Law which holds that $A_\lambda = E_\lambda c l$ Where:
$A_\lambda$=absorbance at wavelength $\lambda$
$E_\lambda$=molar extinction coefficient for a pure substance at wavelength $\lambda$ (which is the amount of light absorbed at wavelength $\lambda$ by 1 mole of material dissolved in one liter of solvent across a 1 cm pathlength)
c=concentration
l=pathlength through the solution Since contaminants, poisons, or biologicals introduced into the reservoir will likely be dissolved and distributed into the contents of the reservoir, the present disclosure operates using algorithms that generate proxy information: spectral attenuation and spectral fluorescence. Spectral attenuation can be calculated from measurements of radiance or irradiance at two locations different distances from the light source. The diffuse attenuation coefficient, $k(\lambda)$, is the rate of attenuation of the light at wavelength $\lambda$ per meter of water:

$$k(\lambda) = -\ln(E1(\lambda)/E2(\lambda)) \cdot (d-1)$$

where $E1(\lambda)$ and $E2(\lambda)$ are light measurements at distances 1 and 2 from the lamp and d is the distance between the two instruments (the pathlength). An advantage in the use of k in measurements of chlorophyll is that it is a sensitive integrator of the conditions of the water column between the two instruments. Spectral fluorescence is a descriptive characteristic of many compounds and is measured directly by the radiometers.

Figure 1:
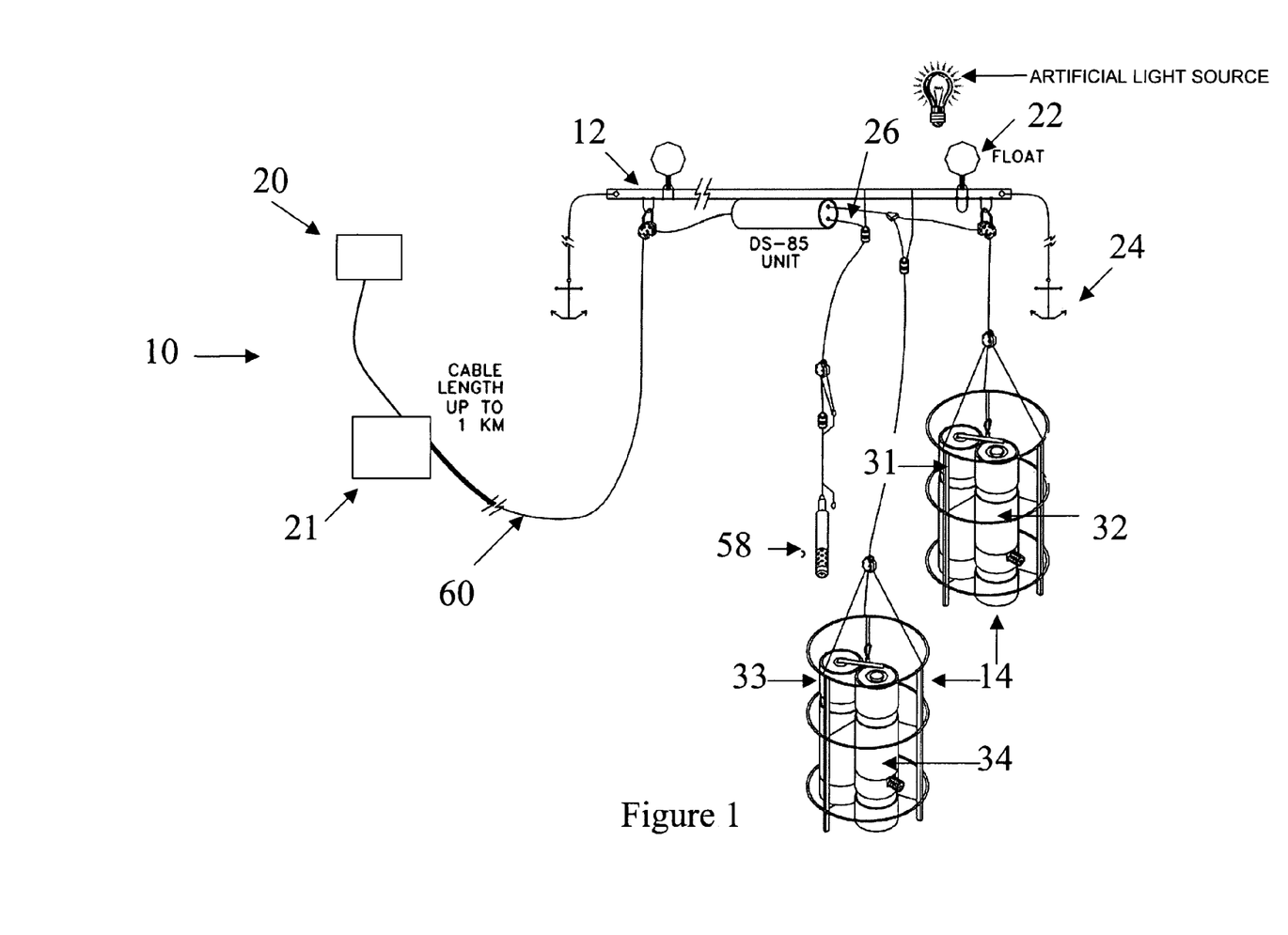
FIG. 1 is an illustrative diagram showing one embodiment of the Defensive Contaminant DEFCON™ system.

FIG. 1 is an illustrative diagram showing one embodiment of the Defensive Contaminant "DEFCON™" monitoring system. The DEFCON™ monitoring system detects poisons, contaminants and biologicals placed deliberately or naturally occurring in an enclosure such as a covered reservoir containing water. DEFCON™ system 10 includes a floating assembly 12 enabling the system to float on the water surface in the enclosure, an array of underwater measurement devices 14, and a data spooling device (DS) 16 which transmits power to the instrument array and returns monitoring data to a remote access workstation RAW 21 where it is stored and made available to system operators.

Floating assembly 12 includes one or more surface floats 22. Surface floats 22, in this exemplary embodiment, are stabilized by anchors 24. Floating assembly 12 enables an array of measurement devices 14 and DS device 16 to float on the water surface so that measurements are unaffected by the changing volume of stored water. Floating assembly 12 is constructed of stainless steel to minimize corrosion. Floating assembly 12 utilizes submersible cabling including 18-10 SO neoprene coated cables 26.

The array of measurement devices includes either one multiband radiometer (MR) or more than one multiband radiometers (MRs). In FIG. 1, MR 32 and MR 34 are shown. Each MR may have an optional wiper to clean an MR optical window. MR 32 has a wiper 31 to clean the optical window of MR 32. MR 34 has a wiper 33 to clean the optical window of MR 34. The MRs are designed to measure the flux of artificial light absorbed and/or fluoresced by poisons, contaminants, biologicals and other harmful agents. The MRs take measurements of either spectral radiance or irradiance. These measurements support the calculation of attenuation coefficients at selected ultraviolet through visible (UV-VIS) wavebands. In particular, the MRs measure spectral radiance or irradiance using a flat plate collector with 2 pi steradians solid angle. The flat plate collector is a cosine collector specifically designed to achieve a response that is proportional to the cosine of the angle of the incident light.

Each MR includes a total of 19 radiance or irradiance channels viewed through a common cosine collector. In addition, the MRs also measure temperature and pressure/depth. MR 32 is located near the surface of the enclosure whereas MR 34 located anywhere below MR 32 including being placed on the bottom of the enclosure.

The array of underwater measurement devices may include sensors 58 for measuring pH, oxidation/reduction potential, conductivity, and the like.

Data acquisition, system power and telemetry requirements are performed by RAW 21. RAW 21 is designed for unattended system operations. RAW 21 includes a microprocessor based computer system housed in a weatherized enclosure. Specially developed software retrieves the measurement data that includes acquiring, averaging and storing all sensor data as voltages on a programmed schedule. At least two files are acquired each day: a data file consisting of a given time period, averages for each measured variable and a log file showing the general operation status of the system. A central domain controller polls RAW 21 in various locations on a programmed schedule and transfers the data and log files using commercially available software programs through wired or wireless communication devices. The voltage data is converted to engineering units in an ACCESS™ database.

DS device 16 relays power to the instrumentation package and return data through cable 60 connected to RAW 21. Cable 60 is a dual conductor, armored steel hydro wire cable.

In addition, it is within the spirit and scope of the present disclosure to include surface MR 20 to measure radiance or irradiance at the water surface. DS device 16 and surface MR 20 are connected to RAW 21.

The present disclosure differs from the REOS system of the '570 Patent in at least five fundamental ways: (1) the present disclosure is placed in the vicinity of an artificial light source that provides illumination twenty-four hours per day in the near ultraviolet/visible portion of the electromagnetic spectrum between 200–800 nm, (2) the present disclosure measures radiance or irradiance at 19 discrete wavebands between 200–800 nm, (3) the present disclosure is designed to detect a variety of poisons, contaminants and biologicals, (4) the present disclosure utilizes no algorithms that require site specific tuning, and (5) the present disclosure utilizes a reference table of absorption/emission spectra to differentiate a variety of poisons, contaminants and biologicals.

Figure 2:
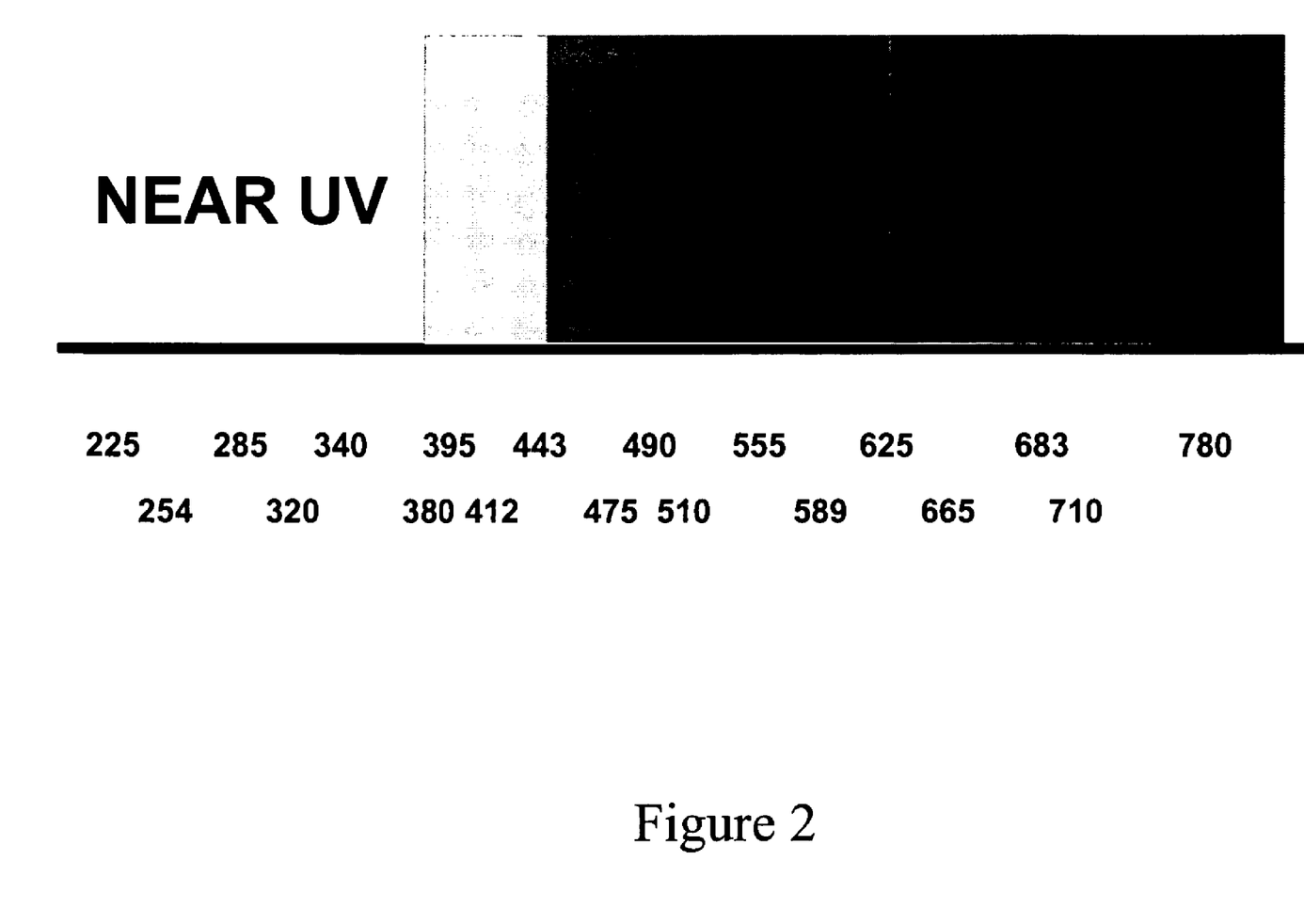
FIG. 2 is a chart of proposed wavebands for detecting and differentiating poisons, contaminants and biologicals.

FIG. 2 is a chart of one set of proposed DEFCON™ wavebands for detecting and differentiating poisons, contaminants and biologicals using sunlight. The DEFCON™ system is designed to be a broadband detector of all poisons, contaminants, and biologicals that absorb or emit light. Prior monitoring systems utilize empirical equations that require site specific tuning to detect and estimate the concentration of chlorophyll in the water column whereas the DEFCON™ system utilizes simple attenuation coefficients and other primary optical measurements in combination with a reference table of absorption and emission spectra to detect and differentiate a variety of poisons, contaminants and biologicals.

Beer's Law holds that the amount of light absorbed by a dissolved substance across a particular waveband is proportional to the molar extinction coefficient for that waveband, the concentration of the solution and the distance that the measured light travels through the solution.

Figure 3:
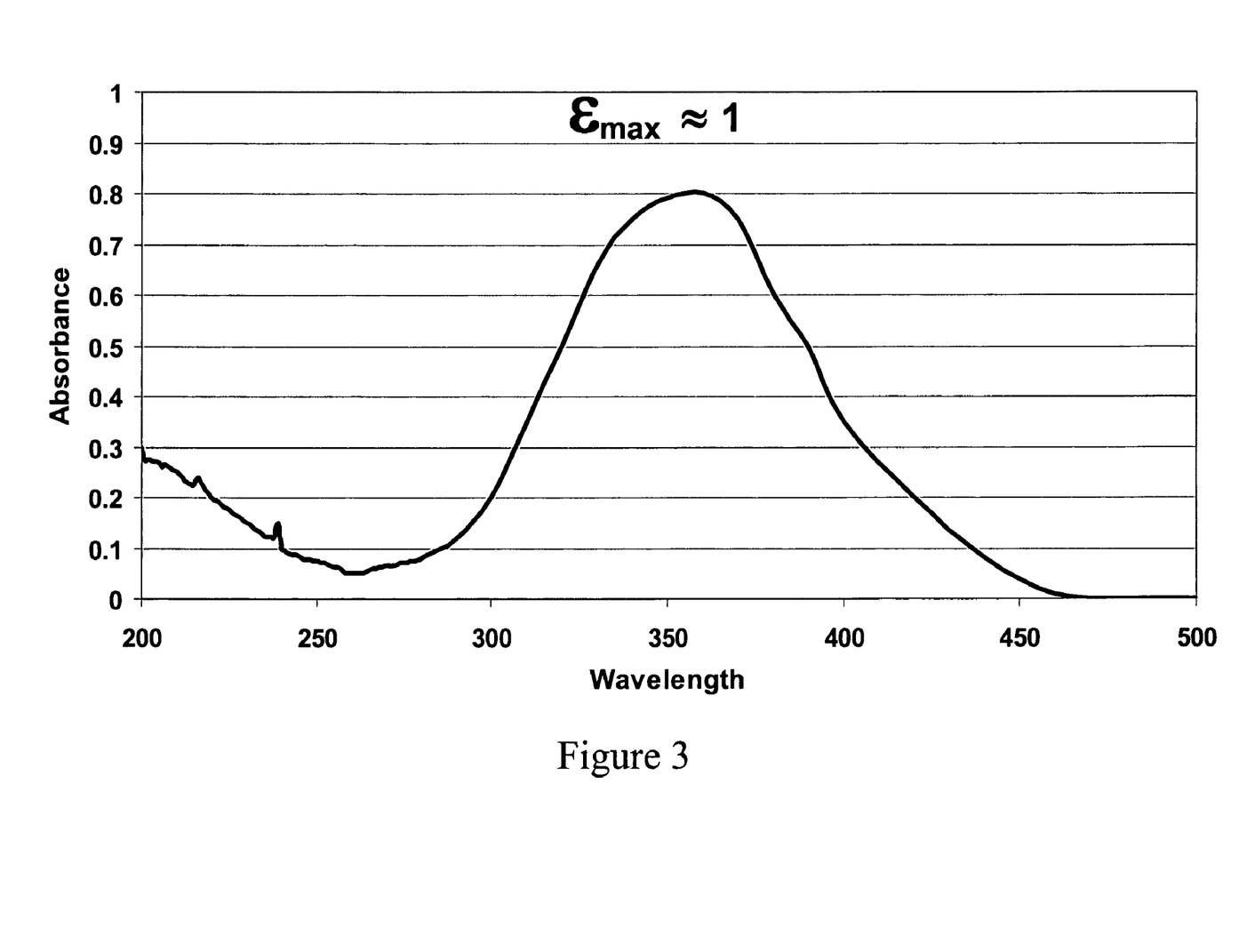
FIG. 3 is a chart showing the ultra violet through visible (UV-VIS) absorption spectrum of chlorine dioxide.

FIG. 3 is a chart showing the ultra violet through visible (UV-VIS) absorption spectrum of chloride dioxide. More specifically, the chart illustrates the absorption spectrum that the water disinfectant chlorine dioxide absorbs light weakly between 275–460 nm with peak absorbance centered near 360 nm.

Figure 4:
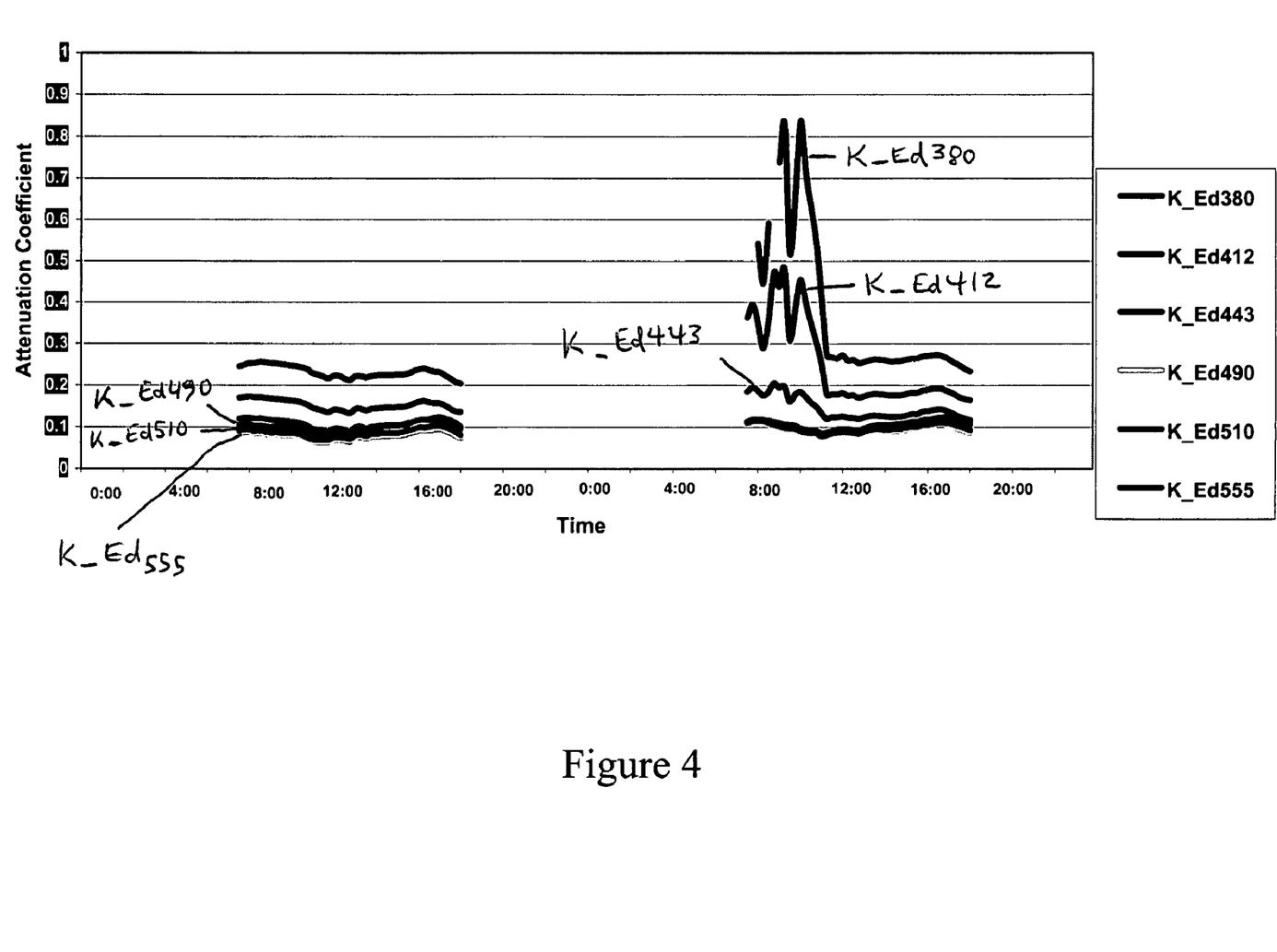
FIG. 4 is an illustrative diagram of the observed effect of chlorine dioxide on the attenuation coefficients at 380, 412, 443, 490, 510 and 555 nm.

FIG. 4 shows the spectral attenuation coefficients measured before and after a nighttime chlorine dioxide treatment of an uncovered reservoir. A nighttime data gap exists. Prior to the nighttime application of chlorine dioxide to the reservoir, the attenuation coefficients at 380, 412, 443, 490, 510 and 555 nm were low and stable. The morning after the application, the attenuation coefficients at 380, 412 and 443 nm were elevated. Consistent with the chlorine dioxide absorption spectrum, as shown in FIG. 3, the 380 nm attenuation coefficient was the most affected.

By contrast, the attenuation coefficients at 490, 510 and 555 nm were unchanged, as expected from FIG. 3. The chlorine dioxide concentration at the time the mid-morning attenuation peaks were observed was 0.25 mg/L. This chlorine dioxide concentration level is equivalent to about 2 pounds of material in a one million gallon tank. The distance the light travels through the chlorine dioxide solution, which is equivalent to the distance between the two radiometers, is about 3 meters. Even greater sensitivity could be achieved by increasing the distance the measured light travels through the chlorine dioxide solution (the pathlength) by moving the radiometers to increase the distance between them.

Figure 5:
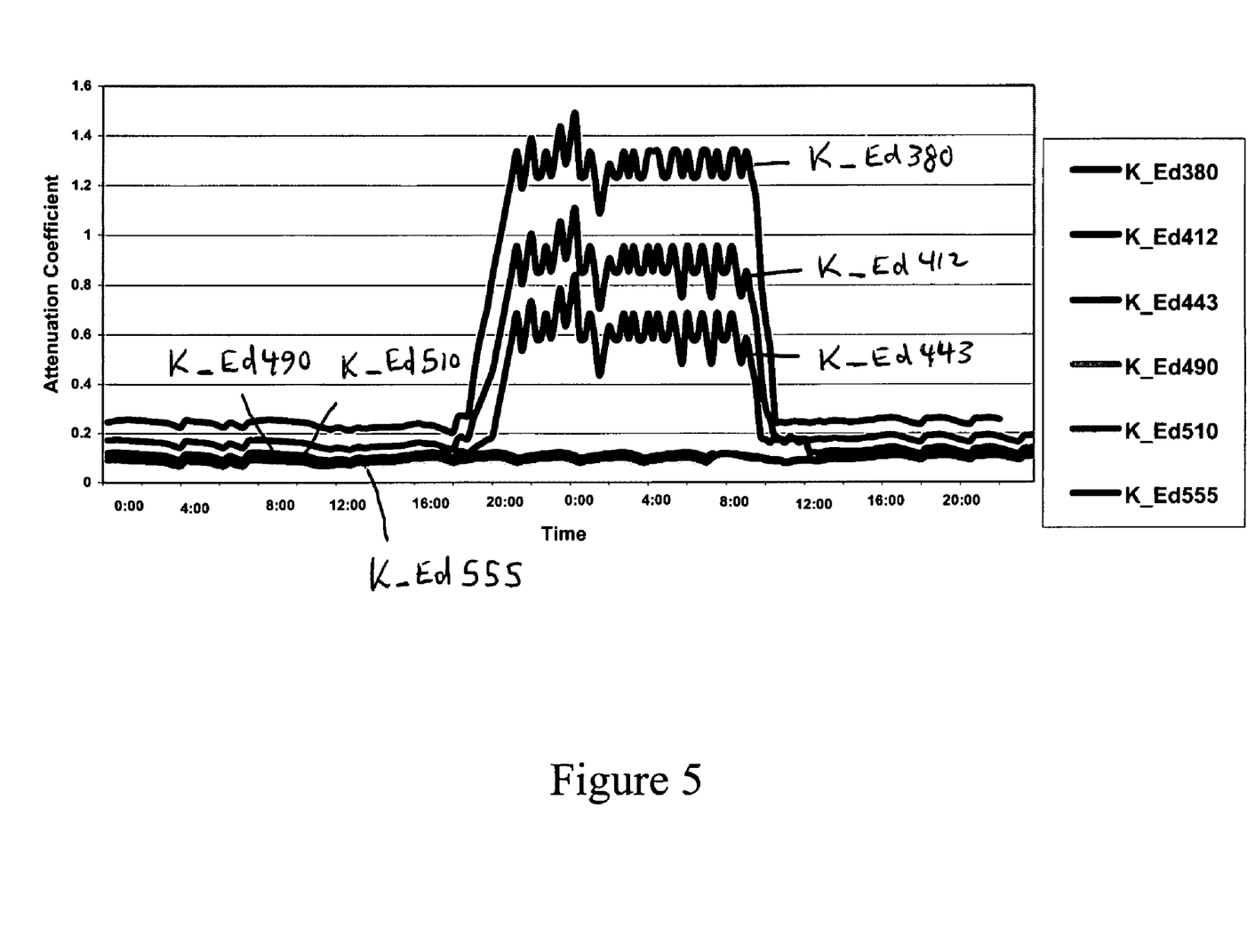
FIG. 5 is an illustrative diagram of the expected effect of chlorine dioxide on the attenuation of coefficients at 380, 412, 443, 490, 510 and 555 nm utilizing the present disclosure.

FIG. 5 shows how the spectral attenuation measurements made by the present disclosure under the constant illumination of an artificial light source would be expected to reveal the actual time of application of the chlorine dioxide. The present disclosure can be used to continuously monitor water quality twenty-four hours a day.

Figure 6:
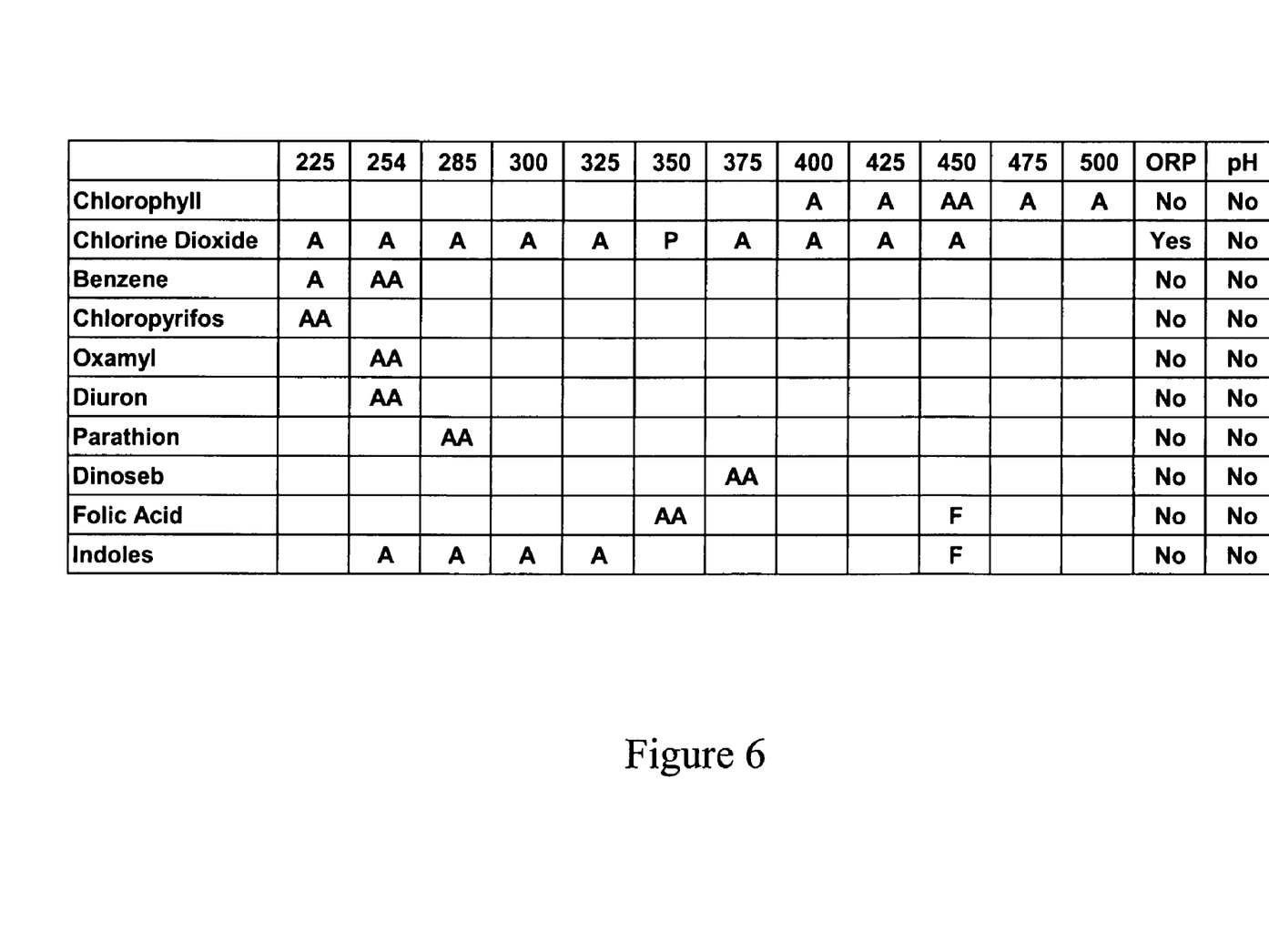
FIG. 6 is a chart of light absorption and emission wavebands for different materials.

Many substances absorb and/or emit UV-VIS light. FIG. 6 is a chart setting forth details regarding the absorption and emission spectra of some representative compounds at different wavebands. This is especially true of organic compounds and standard reference works provide spectral absorption and emission data that can be directly applied to the present disclosure. In FIG. 6, A stands for absorption and AA stands for peak absorption; F stands for fluorescence. Chlorophyll is an organic photosynthetic pigment. Benzene is a cyclic organic petroleum product. Chloropyrifos, oxamyl, diuron, parathion, and dinoseb are organic pesticides. Folic acid is an organic vitamin. Indoles are a class of heterocyclic organic petrochemicals.

FIG. 6 shows that wide ranges of organic substances absorb and/or emit UV-VIS light in characteristic ways and that spectral data are useful in both the detection and differentiation of different chemical compounds. Approximately three quarters of the substances on the Federal List of Drinking Water Contaminants are organic compounds. Organic poisons used as terror agents include sarin, tabin, soman, VX nerve agent, and lysergic acid (LSD).

Figure 7:
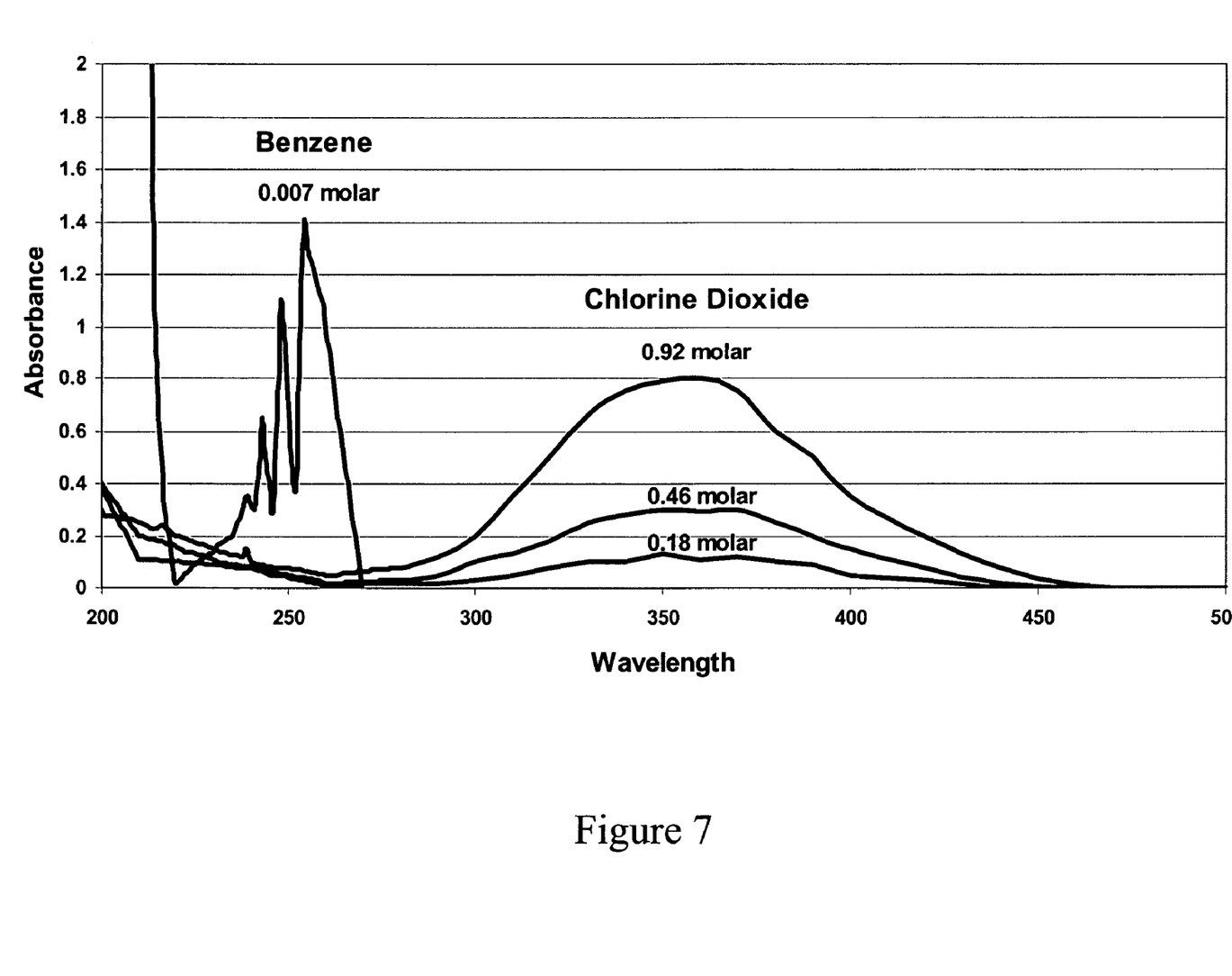
FIG. 7 is a chart comparing the ultra violet through visible absorption spectra of benzene and chlorine dioxide.

The absorption spectra shown in FIG. 7 further demonstrate the sensitivity that can be expected from the present disclosure. The simple, cyclic, conjugated double bond structure of benzene is referred to as a "chromophore" because it absorbs the electromagnetic energy associated with a particular region of the UV-VIS spectrum and it is a common building block of more complex organic molecules. In this example, the maximum absorbance of benzene occurs at 254 nm. Although absorbing much more strongly than chlorine dioxide, which has a maximum molar extinction coefficient of about one ($\in_{360}$~1) at 360 nm, the benzene molecule is still considered to be a relatively weak chromophore because it has a molar extinction coefficient of only 212 at peak absorbance ($\in_{254}$=212). The molar extinction maxima of the slightly more complex molecules naphthalene ($\in_{275}$=6,000) and anthracene ($\in_{356}$=9,700) are much larger, making them even easier to detect by the present disclosure than benzene.

Figure 8:
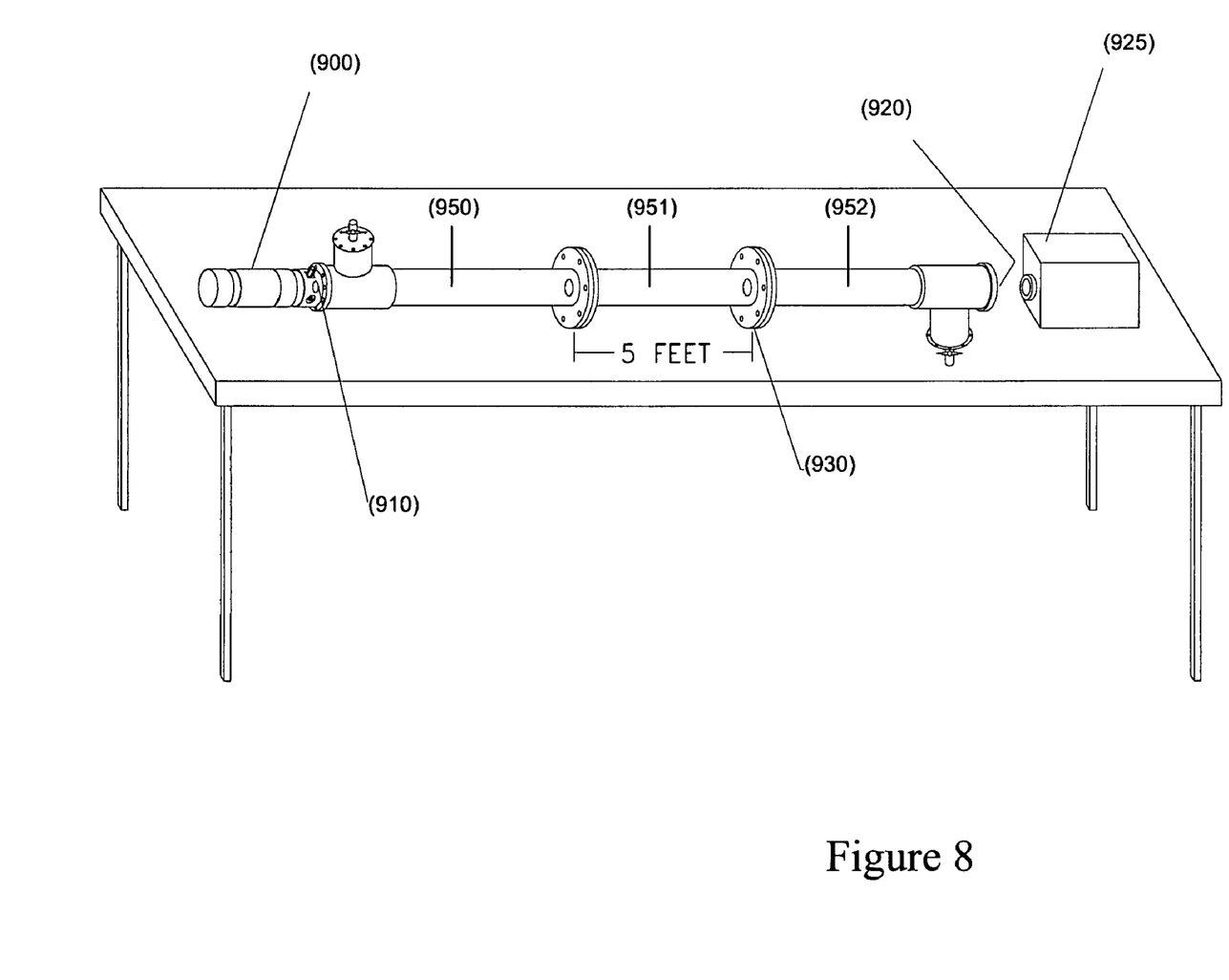
FIG. 8 is an illustration of a laboratory apparatus of the present disclosure.

FIG. 8 is a diagram illustrating a laboratory embodiment of the present disclosure when used to detect poisonous substances. Three, 5 foot sections 950, 951, 952 of plastic piping, connected with flanges 930 that are fitted with light baffles, are used to hold a sample of reservoir water. A multichannel UV sensor 900, such as a multiband radiometer, is used to measure spectral changes in the flux from a high-intensity discharge UV lamp 925 through two quartz windows (910 and 920) along the length of the apparatus. These changes are used to calculate the spectral attenuation coefficient for the sample.

Figure 9:
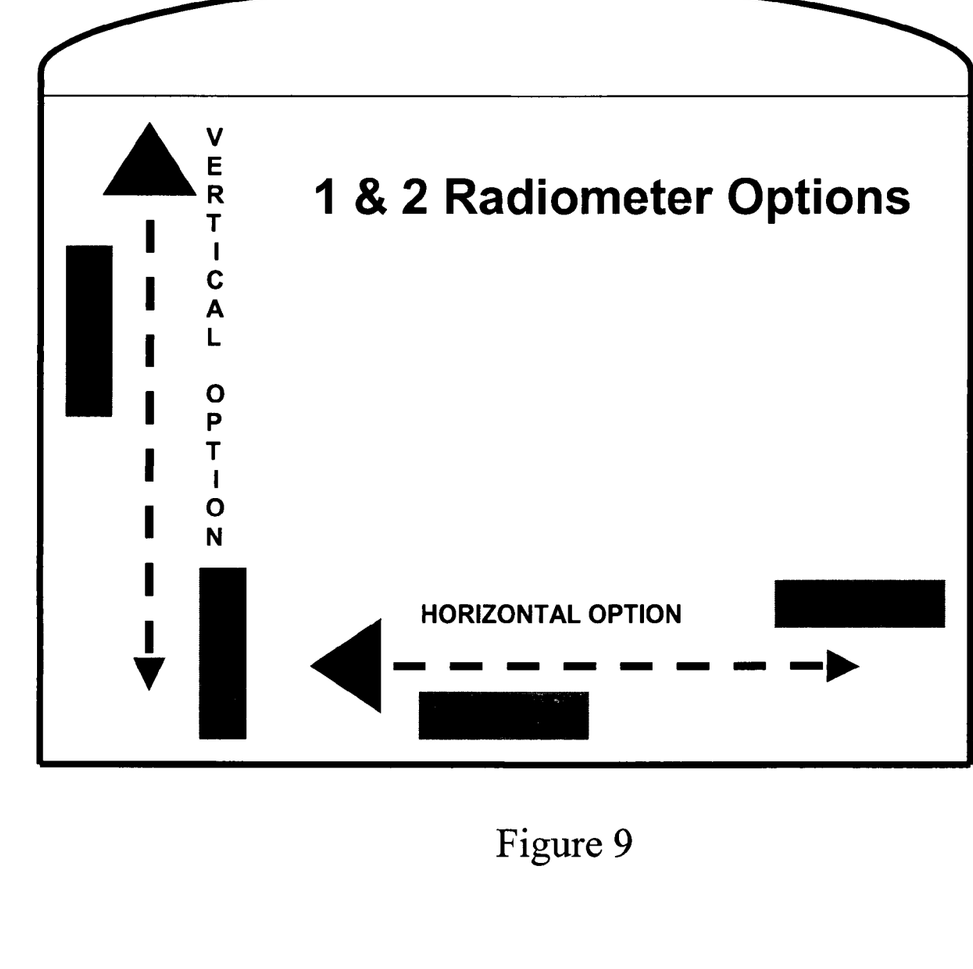
FIG. 9 is an illustration of the system in a tank.

FIG. 9 is an example of the present disclosure illustrating that the system can be configured to use one or more radiometers positioned either vertically or horizontally in the reservoir. If a single radiometer is used, the results report relative changes in the optical properties of the reservoir. If two radiometers are used, the results return more absolute terms.

Figure 10:
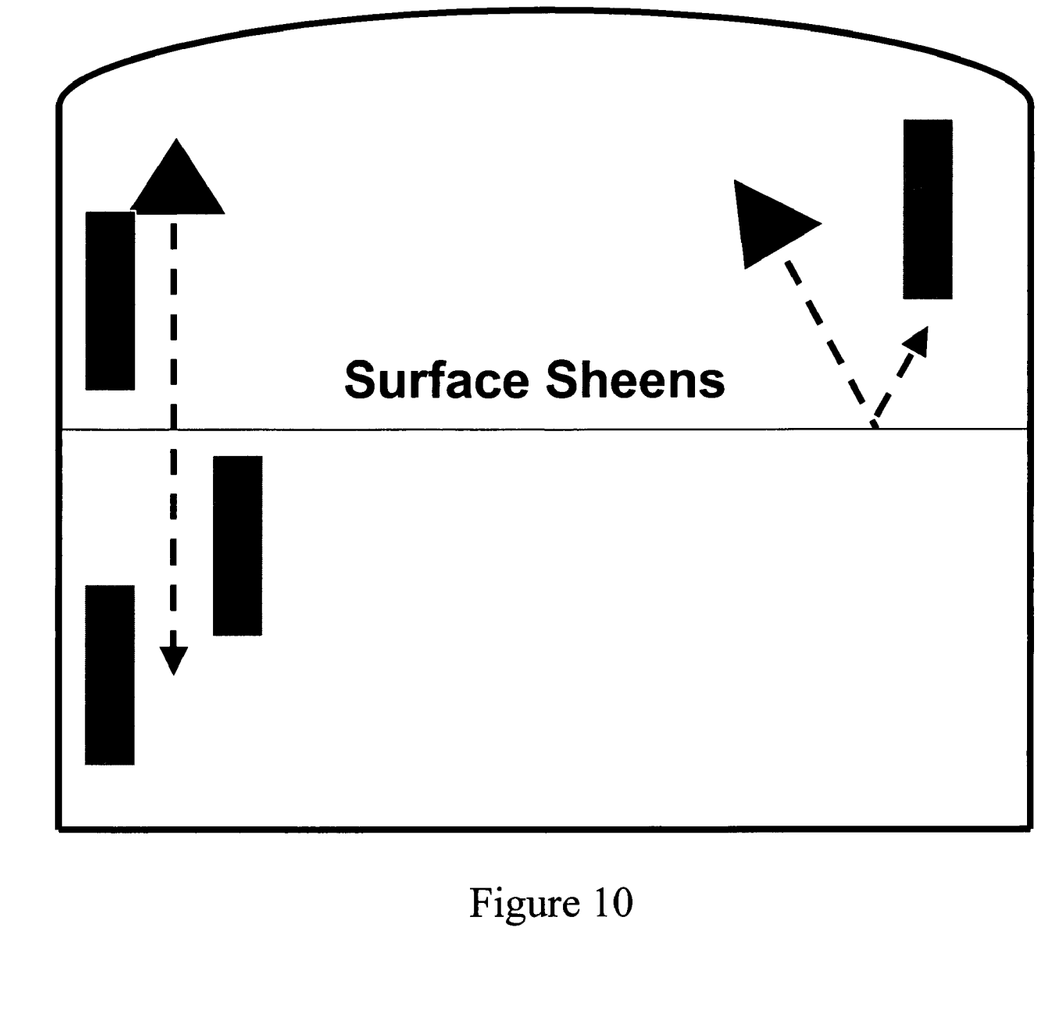
FIG. 10 is an illustration of various options of the present disclosure in a tank.

FIG. 10 is an example of the present disclosure illustrating that the system can be configured with the lamp above the water, thereby affording detection of surface sheens as well as changes in the materials dissolved or suspended in a covered reservoir.

As illustrated by FIGS. 9 and 10, the present disclosure can be used with a single radiometer or with multiple radiometers separated by a known distance. In the vertical option illustrated in the left portion of FIG. 10, an artificial light source illustrated by the larger triangle illuminates the water column in the direction shown with the vertical dashed lines and the solid arrow. In the horizontal option illustrated in the right portion of FIG. 9, a submerged light source illuminates the water column along the path shown with horizontal dashed lines and the solid arrow. Thus, the light source may be moved in relationship to the multiband radiometer to afford greatest sensitivity. The radiometer may be located above the water, at the bottom of the reservoir, or strategically located anywhere within the reservoir.

As illustrated in FIG. 10, it is also possible to have three radiometers arranged beneath an above-water light source such that one radiometer is above and two below the surface of the water. The above-water light source can also be used to direct reflected light from the water surface to an above-water radiometer to detect surface sheens such as those caused by petroleum products.

Therefore, through use of the present disclosure, numerous poisons, contaminants and biologicals can be quickly detected on a continuous near real time basis to provide security and insure the integrity of the nation's water supply.

Of course, the present disclosure is not intended to be restricted to any particular form or arrangement, or any specific embodiment, or any specific use disclosed herein, since the same may be modified in various particulars or relations without departing from the spirit or scope of the claimed disclosure. The apparatus or method shown is intended only for illustration and for disclosure of an operative embodiment and not to show all of the various forms or modifications in which the present disclosure might be embodied or operated.

The present disclosure has been described in considerable detail in order to comply with the patent laws by providing fill public disclosure of at least one of its forms. However, such detailed description is not intended in any way to limit the broad features or principles of the present disclosure, or the scope of the patent to be granted.

We claim:

1. A method for monitoring optical properties of water within a reservoir, the method comprising
    illuminating water within a reservoir with a light source for detecting a substance;
    measuring a change in optical flux along a path-length within the water using a multiband radiometer;
    calculating the attenuation coefficient from the change in the optical flux;
    comparing the attenuation coefficient to typical absorption and emission spectra of the substance for identification of the substance.

2. A method of claim 1, further comprising the steps of:
    measuring a fluorescence spectra, and
    comparing the fluorescence spectra to a typical emission spectra of the substances for identification of the substance.

3. A method of claim 1 wherein the light source is ultraviolet light.

4. A method of claim 1 wherein the reservoir is covered.

5. A method of claim 1 wherein the change in the optical flux is acquired and available in essentially real-time.

6. A method of claim 1 wherein the light source operates essentially continuously.

7. A method of claim 1 wherein the multiband radiometer measures discrete wavebands between 200 nm and 800 nm.

8. A method of claim 1 wherein the multiband radiometer measures continuous wavelengths between 200 nm and 800 nm.

9. A method of claim 1 wherein the comparing step further includes utilizing a reference table of absorption and emission spectra for the substance.

10. A method of claim 1 wherein the substance is selected from the group comprising a contaminant, a poison, and a biological.

11. A system for detecting the presence of a substance in a liquid in an enclosure including:
    an artificial illumination source for illuminating a liquid containing a substance to create optical flux;
    a first multiband radiometer located proximal to the artificial illumination source for detecting changes in the optical flux in one section of an enclosure; and
    a second multiband radiometer located distal to the artificial illumination source for detecting changes in optical flux in a second section of the enclosure; and
    whereby the difference in optical light received by a first multiband radiometer collector and a second radiometer collector is independent of changes in a level of the artificial illumination source.

12. The system of claim 11 wherein the first multiband radiometer is located near a surface of the enclosure and the second multiband radiometer is located below the first multiband radiometer.

13. The system of claim 11 wherein the multiband radiometers measure the optical flux in an electromagnetic spectrum between 200 nm and 800 nm.

14. The system of claim 11 wherein the substance is selected from the group consisting of a contaminant, a poison, and a biological.

15. The system of claim 11 wherein the artificial illumination source provides ultraviolet light.

16. The system of claim 11 further comprising a third multiband radiometer where at least one of the multiband radiometers is located above a surface of the liquid.

17. The system of claim 11 wherein the artificial illumination source is submerged.

18. A method for detecting changes in a level of contaminants in a liquid in a closed reservoir, comprising illuminating a column of liquid in a closed reservoir with an artificial light source for essentially continuously monitoring of the closed reservoir;

measuring the radiance and irradiance in the column of liquid;

calculating the spectral attenuation coefficient of the column of liquid;

comparing the attenuation coefficient with a reference table of absorption and emission spectra for a substance; and determining if the column of liquid contains the substance.

* * * * *